(12) United States Patent
Gordon et al.

(10) Patent No.: US 10,994,100 B2
(45) Date of Patent: *May 4, 2021

(54) SHEATH RETAINER DEVICES, SYSTEMS AND METHODS

(71) Applicant: Radux Devices, LLC, Omaha, NE (US)

(72) Inventors: Gregory Gordon, Omaha, NE (US); Douglas Scott Wahnschaffe, Monticello, MN (US)

(73) Assignee: Radux Devices, LLC, Omaha, NE (US)

( * ) Notice: Subject to any disclaimer, the term of this patent is extended or adjusted under 35 U.S.C. 154(b) by 19 days.

This patent is subject to a terminal disclaimer.

(21) Appl. No.: 16/159,161

(22) Filed: Oct. 12, 2018

(65) Prior Publication Data

US 2019/0038875 A1    Feb. 7, 2019

Related U.S. Application Data

(63) Continuation of application No. 14/854,930, filed on Sep. 15, 2015, now Pat. No. 10,099,037.

(51) Int. Cl.
*A61M 25/02* (2006.01)
*A61M 25/00* (2006.01)
(Continued)

(52) U.S. Cl.
CPC ........ *A61M 25/02* (2013.01); *A61M 25/0026* (2013.01); *A61M 25/0052* (2013.01); *A61M 25/01* (2013.01); *A61M 39/06* (2013.01); *A61M 25/0108* (2013.01); *A61M 2025/0059* (2013.01); *A61M 2025/024* (2013.01); *A61M 2025/028* (2013.01); *A61M 2025/0266* (2013.01);
(Continued)

(58) Field of Classification Search
CPC .............. A61M 25/02; A61M 25/0052; A61M 25/0026; A61M 25/01; A61M 25/0108; A61M 39/06; A61M 2025/0059; A61M 2025/024; A61M 2025/0266; A61M 2025/028; A61M 2039/0626; A61M 2039/066; A61M 2205/586
See application file for complete search history.

(56) References Cited

U.S. PATENT DOCUMENTS 3,853,126 A   12/1974   Schulte
3,998,222 A   12/1976   Shihata
(Continued)

OTHER PUBLICATIONS

Dr. Gregory Gordon, Radux Devices, LLC, "Demo Day 2013: Radux," You Tube [online]. Retrieved from the Internet: <URL: https://www.youtube.com/watch?v=SsZhtA7heJE>, published on Nov. 26, 2013, [16 minute video submitted on disk].
(Continued)

*Primary Examiner* — Nathan R Price
*Assistant Examiner* — John A Doubrava
(74) *Attorney, Agent, or Firm* — Fish & Richardson P.C.

(57) ABSTRACT

In general, medical sheath systems that can employ retainer devices having a plurality of channels configured to retain a sheath assembly in one or more curved configurations are described. In one embodiment, a retainer device may releasably retain a curvable tube of the sheath assembly in any of multiple curved configurations that range, for example, in selectable increments between 0° to 180°.

22 Claims, 6 Drawing Sheets

(51) Int. Cl.
*A61M 39/06* (2006.01)
*A61M 25/01* (2006.01)

(52) U.S. Cl.
CPC ............ *A61M 2039/066* (2013.01); *A61M 2039/0626* (2013.01); *A61M 2205/586* (2013.01)

(56) References Cited

U.S. PATENT DOCUMENTS

| | | |
|---|---|---|
| 4,029,103 A | 6/1977 | McConnell |
| 4,316,461 A | 2/1982 | Marais et al. |
| 4,453,933 A | 6/1984 | Speaker |
| 4,585,435 A | 4/1986 | Vaillancourt |
| 4,840,613 A | 6/1989 | Balbierz |
| 4,850,954 A | 7/1989 | Charvin |
| 4,865,586 A | 9/1989 | Hedberg |
| 4,976,698 A | 12/1990 | Stokley |
| 5,031,775 A | 7/1991 | Kane |
| 5,357,961 A * | 10/1994 | Fields .............. A61M 25/0102 600/435 |
| 5,407,434 A | 4/1995 | Gross |
| 5,443,460 A | 8/1995 | Miklusek |
| 5,538,513 A | 7/1996 | Okajima |
| 5,647,859 A | 7/1997 | Lampropoulos et al. |
| 5,902,274 A | 5/1999 | Yamamoto et al. |
| 5,916,199 A | 6/1999 | Miles |
| 5,947,931 A | 9/1999 | Bierman |
| 5,989,223 A | 11/1999 | Chu et al. |
| 6,001,081 A | 12/1999 | Collen |
| 6,113,577 A | 9/2000 | Hakky et al. |
| 6,179,828 B1 | 1/2001 | Mottola |
| 7,198,066 B2 | 4/2007 | Kagenow |
| 7,553,326 B2 | 6/2009 | Sweet |
| 7,571,744 B2 | 8/2009 | Zia |
| 8,911,396 B2 | 12/2014 | Gordon |
| 9,585,691 B2 | 3/2017 | Gordon |
| 10,009,903 B2 | 6/2018 | Kim et al. |
| 2001/0053895 A1 | 12/2001 | Vaillancourt |
| 2002/0087108 A1 | 7/2002 | Maginot et al. |
| 2002/0107479 A1 | 8/2002 | Bates et al. |
| 2002/0120224 A1 * | 8/2002 | Zia .................. A61M 5/1418 604/6.16 |
| 2004/0087905 A1 | 5/2004 | Breznock et al. |
| 2004/0147877 A1 | 7/2004 | Heuser |
| 2004/0153021 A1 | 8/2004 | Osborne et al. |
| 2005/0033238 A1 | 2/2005 | Cope et al. |
| 2005/0113799 A1 | 5/2005 | Lenker |
| 2005/0165364 A1 | 7/2005 | DiMatteo |
| 2005/0209584 A1 | 9/2005 | Rome |
| 2005/0234405 A1 | 10/2005 | Dikeman et al. |
| 2006/0009737 A1 | 1/2006 | Whiting et al. |
| 2006/0047266 A1 | 3/2006 | Elkins et al. |
| 2006/0074398 A1 | 4/2006 | Whiting et al. |
| 2006/0084927 A1 | 4/2006 | Formichi |
| 2006/0129091 A1 | 6/2006 | Bonnette et al. |
| 2006/0129112 A1 | 6/2006 | Lynn |
| 2006/0129134 A1 | 6/2006 | Kerr |
| 2006/0155247 A1 | 7/2006 | Lampropoulos |
| 2007/0161956 A1 | 7/2007 | Heuser |
| 2007/0167901 A1 | 7/2007 | Herrig et al. |
| 2007/0225680 A1 | 9/2007 | Biggins |
| 2008/0171944 A1 | 7/2008 | Brenneman |
| 2008/0195046 A1 | 8/2008 | Altman |
| 2009/0054845 A1 | 2/2009 | Puhasmagi et al. |
| 2009/0306574 A1 | 12/2009 | Kopperschmidt |
| 2010/0030162 A1 | 2/2010 | Cremascoli et al. |
| 2012/0130151 A1 | 5/2012 | Kassab et al. |
| 2013/0006163 A1 * | 1/2013 | Gordon .............. A61B 17/3498 604/8 |
| 2013/0211382 A1 * | 8/2013 | Mouri .............. A61M 25/0133 604/510 |
| 2014/0343531 A1 * | 11/2014 | Larkin .................. A61M 25/02 604/506 |
| 2015/0105752 A1 | 4/2015 | Gordon et al. |
| 2017/0072164 A1 | 3/2017 | Gordon et al. |
| 2017/0136218 A1 | 5/2017 | Gordon |

OTHER PUBLICATIONS

Dr. Gregory Gordon, Radux Devices, LLC, "Radux Devices." 2015 Society of Interventional Radiology Annual Meeting, IR Venture Forum, 15 slides, Mar. 3, 2015.
International Preliminary Report on Patentability in International Application No. PCT/US2010/060556, dated Jun. 19, 2012, 4 pages.
International Search Report and Written Opinion in International Application No. PCT/US2010/060556, dated Aug. 31, 2011, 6 pages.
Kumru et al., "New Prototypes Designed for Interventional Radiology," *UNMC Discover*, Spring 2015, pp. 18-19.
Supplementary European Search Report in EP Application 10842550. 5, dated Nov. 29, 2013, 7 pages.

* cited by examiner

SHEATH RETAINER DEVICES, SYSTEMS AND METHODS

CROSS-REFERENCE TO RELATED APPLICATIONS

This application is a continuation of U.S. application Ser. No. 14/854,930, filed Sep. 15, 2015 know U.S. Pat. No. 10,099,037). The disclosure of the prior application is considered part of (and is incorporated by reference in) the disclosure of this application.

TECHNICAL FIELD

This document describes devices, systems and methods for retaining medical devices, and in some embodiments, retainer devices having a plurality of channels for retaining sheaths in a straight or curved configuration.

BACKGROUND

Radiation protection in the medical field is important, particularly for physicians and healthcare practitioners. Procedures and therapies are often designed to minimize patient exposure while allowing physicians to effectively treat the patient. For example, imaging machines may be designed to decrease patient exposure by implementing lower radiation levels. However, cumulative exposure of physicians and healthcare practitioners may be significant as they often perform multiple treatments in a typical day, and may be increased when a particular treatment requires physicians' hands, for example, to be within a field of radiation.

Healthcare workers using traditional equipment and techniques are often exposed to radiation during patient procedures. For example, physicians' or healthcare practitioners' hands may be exposed to radiation from fluoroscopic imaging equipment when inserting a catheter in a patient's vessel, or when delivering other instruments, medicines, fluids, or other endovascular devices in a patient's vessel. Even when radiation levels may be minimal for a given procedure, cumulative exposure of physicians and healthcare workers can be significant over the course of multiple procedures per day.

Physical barriers have often been used to limit radiation exposure. Radiation shielding and body wear, however, can be bulky and obtrusive. For example, some physical barriers can increase orthopedic stress on the physician or healthcare worker using the body wear and/or inhibit ergonomic efficiency. Some physicians and healthcare workers may forego such physical barriers to avoid one or more of these drawbacks. As a result, physicians and healthcare workers may expose themselves to undesirable levels of radiation.

SUMMARY

In general, this document describes medical sheath systems that can employ retainer devices having a plurality of channels configured to retain a sheath assembly in one or more straight or curved configurations. In one embodiment, a retainer device may releasably retain a curvable tube of the sheath assembly in any of multiple curved configurations that range, for example, in selectable 30° increments between 0° and 180°. As such, a physician or other user can secure the retainer device to a skin surface of a patient and selectively mate the curvable tube with the retainer device so that the curvable tube is retained in a selected curved configuration. Exemplary retainer devices may thus retain a tube in a particular configuration such that the patient can be effectively treated while the physician or healthcare physician operates from outside a radiation field or from an ergonomically desirable position.

Particular embodiments described herein include retainer devices that may be used with a curvable tube to allow positioning of a sheath outside of a radiation field or in a desired ergonomic position. The retainer device maintains the desired positioning of the curvable sheath while treatment is performed. In this way, radiation exposure of physicians and healthcare workers may be reduced or minimized while also improving the ergonomic and orthopedic impact upon the user.

In one aspect, a sheath assembly includes a curvable tube including a first end having a connector and a second end having a port configured to receive an interventional tool, the curvable tube configured to bend between a curved configuration and a substantially straight configuration in which the first end is linearly distal to the second end, and a retainer having a plurality of channels configured to releasably retain the curvable tube in first and second curved configurations, the curvable tube forming a 180° curve when the curvable tube is retained by the retainer in the first curved configuration and forming a 90° curve when the curvable tube is retained by the retainer in the second curved configuration.

Implementations can include any, all, or none of the following features. The plurality of channels may include a first channel defining a first channel axis and a second channel defining a second channel axis, the first channel axis parallel to and offset from the second channel axis. The plurality of channels may include a first channel defining a first channel axis and a second channel defining a second channel axis, the first channel axis being coaxial with the second channel axis. The plurality of channels may include a first channel defining a first channel axis and a second channel defining a second channel axis, the first channel axis angled 90° relative to the second channel axis. The plurality of channels may include a third channel defining a third channel axis, the third channel axis angled 90° relative to the first channel axis. The plurality of channels may include a fourth channel defining a fourth channel axis, the fourth channel axis angled 45° relative to the first channel axis. The plurality of channels may include a fifth channel defining a fifth channel axis, the fifth channel axis coaxial with the first channel axis. The plurality of channels may include a sixth channel defining a sixth channel axis, the sixth channel axis angled 135° relative to the first channel axis. The retainer may include a U-shaped frame. The first and second channels may be spaced along the U-shaped frame. The plurality of channels may be fixedly positioned relative to one another. The plurality of channels may each upwardly open. The retainer may include an adhesive.

In another aspect, a sheath retainer device includes first, second, third and fourth channels configured to releasably retain a curvable portion of a sheath assembly and defining respective first, second, third and fourth channel axes, the second channel axis parallel and offset from the first channel axis, the third channel axis coaxial with the first channel axis, and the fourth channel angled 90° relative to the first channel axis.

Implementations can include any, all, or none of the following features. The sheath retainer device may include a U-shaped frame, the first, second, third and fourth channels spaced along the U-shaped frame. The plurality of channels may be fixedly positioned relative to one another. The plurality of channels may each upwardly open. The sheath device may include a fifth channel defining a fifth channel axis, the fifth channel axis angled 45° relative to the first channel axis.

In another aspect, a sheath assembly includes a curvable tube including a first end having a connector and a second end having a port configured to receive an interventional tool, the curvable tube configured to bend between a curved configuration and a substantially straight configuration in which the first end is linearly distal to the second end, and a retainer having a plurality of channels configured to releasably retain the curvable tube in first and second curved configurations, the plurality of channels including first, second, third and fourth channels defining respective first, second, third and fourth channel axes, the second channel axis parallel and offset from the first channel axis, the third channel angled 90° relative to the first channel axis, and the fourth channel axis coaxial with the first channel axis. The curvable tube forms a 180° curve when portions of the curvable tube are retained by the first and second channels, the curvable tube forms a 90° curve when portions of the curvable tube are retained by the first and third channels, and the curvable tube forms a substantially straight configuration when retained by the first and fourth channels. The sheath device may include a fifth channel defining a fifth channel axis, the fifth channel axis angled 45° relative to the first channel axis.

In another aspect, a medical sheath system includes a catheter having a distal end, a proximal end, and at least one lumen extending between he distal end and the proximal end, and the catheter includes a sealable connector at the proximal end having a septum. The medical sheath system further includes a sheath assembly including a first end having a connector to mate with the proximal end of the catheter and extend through the septum of the catheter, a second end having a septum hub port configured to receive an interventional tool, a curvable tube configured to bend between a curved configuration and a substantially straight configuration in which the first end is linearly distal to the second end, and a side arm extending from the septum hub port and defining a central lumen that extends to a valve device of the side arm, and a retainer configured to secure to a skin surface and having a plurality of channels configured to releasably retain the curvable tube in first and second curved configurations, the plurality of channels including first, second, third and fourth channels defining respective first, second, third and fourth channel axes, the second channel axis parallel and offset from the first channel axis, the third channel angled 90° relative to the first channel axis, and the fourth channel axis coaxial with the first channel axis. The curvable tube forms a 180° curve when portions of the curvable tube are retained by the first and second channels, the curvable tube forms a 90° curve when portions of the curvable tube are retained by the first and third channels, and the curvable tube forms a substantially straight configuration when retained by the first and fourth channels. The retainer includes a fifth channel defining a fifth channel axis, the fifth channel axis angled 45° relative to the first channel axis.

Some embodiments of the devices, systems and techniques described herein may provide one or more of the following advantages. First, retainer devices described herein may reduce physical stress on a physician or healthcare practitioner by allowing positioning of a curvable tube in a selected configuration, which is then retained in the selected configuration, for a particular application or treatment location. Second, a port of a sheath assembly may be positioned outside of a radiation field. In this way, an interventional tool or other component may be introduced by a physician or healthcare practitioner without requiring that their hands be directly exposed to maximum levels of radiation. Similarly, a patient or healthcare practitioner may work at a greater distance away from imaging equipment, reducing potential exposure to their head, neck, and other body parts. Third, retainer devices and/or sheath assemblies described herein may allow improved access to an intervention site for a physician or healthcare practitioner and provide improved control of one or more instruments used with the retainer device and/or sheath assembly. For example, access to both sides of a conduit from the same operator position may be facilitated. Fourth, retainer devices and/or sheath assemblies described herein may serve as an anchor to maintain a catheter and/or sheath assembly in a stable position relative to a patient access opening, and may promote sterility. Fifth, easy positioning of a sheath assembly may reduce treatment times of a particular procedure and improve overall patient care.

The details of one or more implementations are set forth in the accompanying drawings and the description below. Other features and advantages will be apparent from the description and drawings, and from the claims.

DESCRIPTION OF DRAWINGS

The present description is further provided with reference to the appended Figures, wherein like structure is referred to be like numerals throughout the several views, and wherein.

DETAILED DESCRIPTION OF ILLUSTRATIVE EMBODIMENTS

Figure 1:
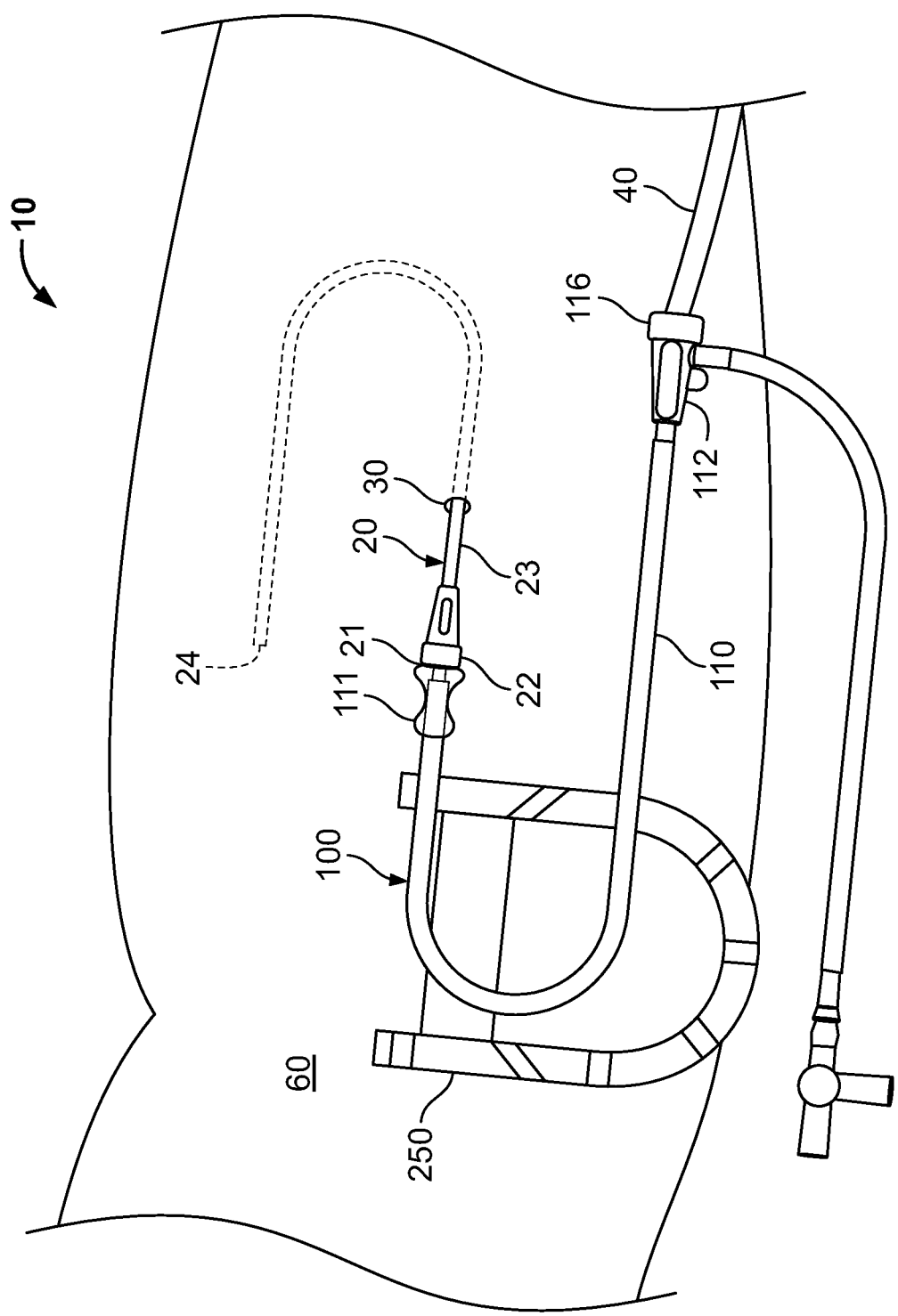
FIG. 1 is a perspective view of a medical sheath system in accordance with some embodiments.
Figure 2A:
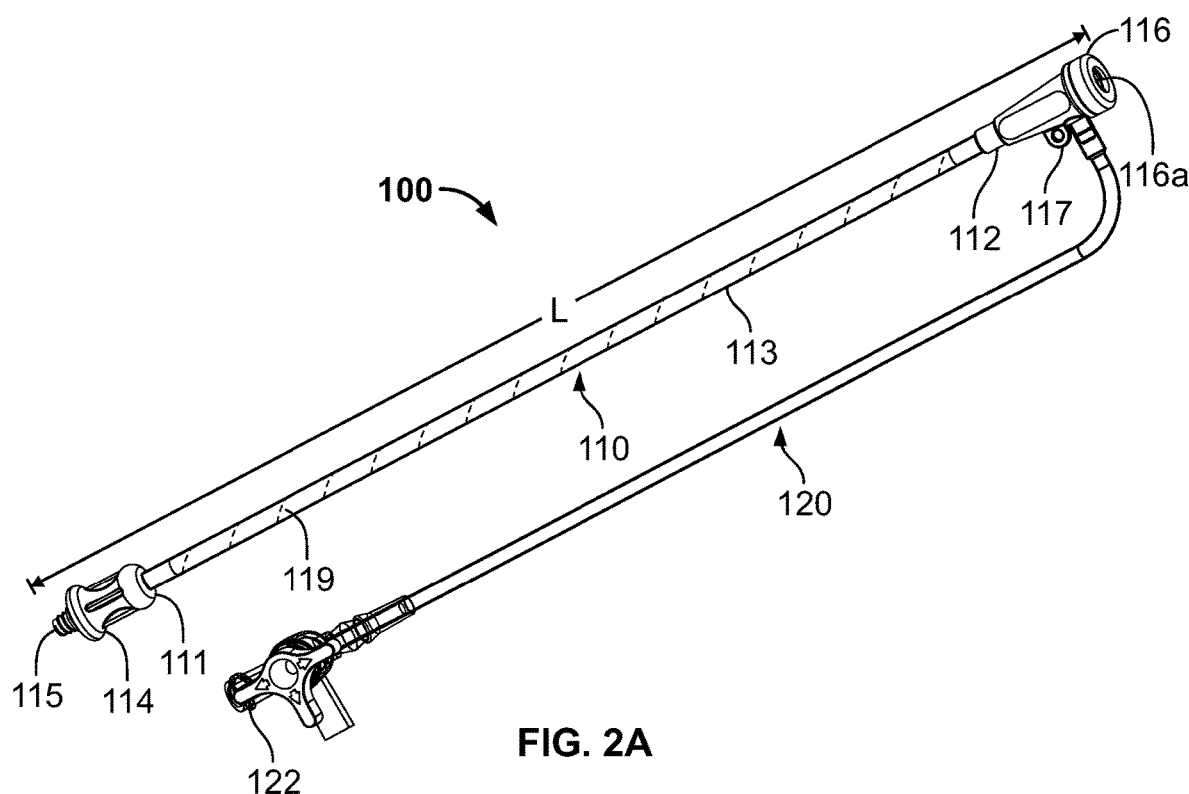
FIGS. 2A and 2B are perspective views of an exemplary sheath assembly including a curvable portion.
Figure 2B:
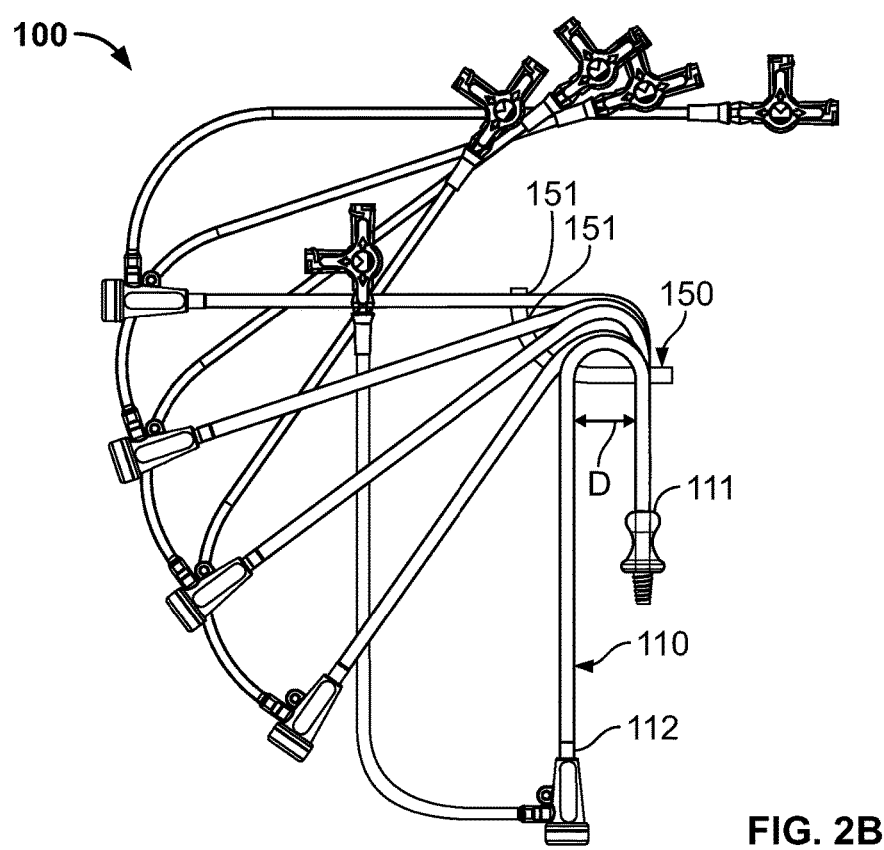

Referring to FIG. 1, some embodiments of a medical sheath system 10 include a sheath assembly 100, a retainer 250 configured to mate with a curvable tube 110 of sheath assembly 100, and optionally, a catheter 20 and medical instrument 40. The system 10 is configured to retain curvable tube 110 in a selected curved configuration and to extend a user's operative location further away from a proximal end 21 of catheter 20 and a radiation field (e.g., caused by a medical imaging system), thereby permitting the physician or healthcare practitioner to operate from outside the radiation field and in a selected ergonomic position while effectively treating the patient. As described in more detail below, sheath assembly 100 in this embodiment is configured to be retained entirely outside the patient's body, and may include a first end 111 and a second end 112 including a sealable port 116 (FIGS. 2A-B). Sealable port 116 allows interventional tool 40 (or other medical instrument) to be passed through curvable tube 110 and into catheter 20 that extends into the patient's body at access point 30. Also as described in more detail below, retainer 250 in this embodiment can be arranged on the exterior of the patient's body (e.g., adhered to the patient's skin 60 or the like), and includes a plurality of retention features (FIGS. 3A-4D) that releasably retain curvable tube 110 in a plurality of curved configurations. In this way, retainer 250 maintains the curvable tube in a user-selected configuration from a plurality of predetermined configurations to enhance the ergonomic position of the physician or other user while also providing an anchoring effect to reduce the likelihood of unintended withdrawal of catheter 20 or sheath assembly 100.

Catheter 20 may be any suitable access sheath, vascular sheath, or suitable endovascular medical device, and is configured to extend through a perforation in a side wall and into an anatomical conduit, such as a blood vessel. In an exemplary embodiment, catheter 20 has a proximal end 21, a distal end 24, and at least one lumen 23 extending between the proximal and distal ends 21, 22, and defines a pathway for delivery or withdrawal of fluids, instruments such as guide wires or other interventional tools, or a combination thereof. Catheter 20 includes a sealable connector having a septum 22 external to a patient's skin 60 that is configured to releasably mate with first end 111 of sheath assembly 100. One or more lumens 23 may extend just under the skin, and have a length between 2 cm and 10 cm, for example, or may extend a greater distance into a patient, and have a length between 10 cm and 100 cm or more, for example.

Referring now to FIGS. 2A and 2B, an exemplary sheath assembly 100 according to the present description is illustrated. Sheath assembly 100 includes a curvable tube 110 and a side arm 120. In an exemplary embodiment, curvable tube 110 provides access to a catheter, for example, such as an introducer sheath or other vascular access component, and provides a support sheath extension that may be used at a vascular access site.

Curvable tube 110 includes a first end 111, second end 112 and an elongate portion 113. Elongate portion 113 defines a central passage or lumen through which an interventional tool, medicine, or other suitable component may be delivered to or extracted from a vascular access site. First end 111 may include a connector end configured to be joined with a hemostasis valve or other port or connector of a catheter 20 (FIG. 1), such as an introducer sheath or other intravenous access component. Second end 112 may include a port 116 providing an opening 116a for an interventional tool, medicine or other suitable component to be passed through curvable tube 110 and into a patient access site.

In an exemplary embodiment, first end 111 includes a connector, such as an adapter 114. Adapter 114 may be removably or permanently joined to first end 111 and includes one or more attachment features 115 configured to couple with the catheter, for example. Adapter 114 may be removably or permanently attachable to allow communication between curvable tube 110 and the catheter. In an exemplary embodiment, attachment features 115 include helical threads compatible with one or more introducer sheaths, such as the GLIDESHEATH introducer sheath available from Terumo Medical Corporation, SUPER SHEATH introducer sheath available from Boston Scientific Corporation, INPUT introducer sheath available from Medtronic, other introducer sheaths, or suitable components providing vascular access to a patient for the introduction of an interventional tool, medicine, or other suitable component. In various exemplary embodiments, attachment features 115 may include a luer lock connector, bayonet connector, snap connector, or other suitable attachment feature to allow secure connection between adapter 114 and the catheter. In some exemplary embodiments, adapter 114 is configured for attachment to a second end 112 of curvable tube 110, for example at port 116, such that two or more curvable portions may be connected in series. In an exemplary embodiment, adapter 114 has a widened body to facilitate handling and that may be thicker than elongate portion 113. In some embodiments, the widened body may have a curved surface or one or more features such as texture, ribs, etc. to facilitate handling.

Second end 112 of curvable tube 110 includes a port 116, such as a septum hub port. Port 116 includes at least a first opening 116a for insertion of an interventional tool that may be passed through curvable tube 110, through a component attached at first end 111, and/or into a patient access location, and may include a hemostasis valve. In some exemplary embodiments, port 116 includes a suture connector 117 defining an opening that one or more sutures may be passed through to secure port 116 and second end 112 of curvable tube 110 in a desired location.

In an exemplary embodiment, port 116 defines a septum hub that a side arm 120 may be attached to. Side arm 120 defines a central lumen and may include one or more valve devices or other components, such as a three-way stop cock 122. Side arm 120 may be used to aspirate air and blood and allow for improved suction and/or aspiration of the thrombus/clot. In an exemplary embodiment, side arm 120 may flex and bend without kinking or substantially blocking the central lumen, and for example may bend at least between a substantially straight configuration and a configuration forming a 180° curve, 90° curve or 45° curve.

In an exemplary embodiment, side arm 120 includes a valve or other component, such as three-way stop cock 122, that may allow infusion of contrast, saline solution, or other component, aspiration, collection of blood or other sample, or passage to curvable tube 110 and an access point of a patient. In some exemplary embodiments, three-way stop cock 122, side arm 120 and/or other suitable components of sheath assembly 100 are suitable for high pressure applications. For example, three-way stop cock 122, side arm 120 and/or other suitable components may be suitable for applications requiring pressures between 400 psi and 1000 psi, 600 psi and 900 psi, 700 psi and 850 psi, or about 800 psi.

Curvable tube 110 may have any suitable length as desired for a particular application or procedure. In an exemplary embodiment, curvable portion has a length (L) between first and second ends 111, 112 between approximately 5 cm and 50 cm, 10 cm and 40 cm, 15 cm and 30 cm, or about 20 cm. Such a length (L) provides a curvable tube 110 that is sufficiently compact to exhibit desirable stability, while sufficiently long to allow flexibility in positioning and configuration such that a physician or healthcare practitioner may operate outside of a direct field of radiation or in an ergonomically desirable position. In various exemplary embodiments, sheath assembly 100, and curvable tube 110, are compatible with any suitable French system devices, for example up to 28 French devices, 24 French device, 12 French devices, or between about 5 and 8 French system devices.

In an exemplary embodiment, curvable tube 110 is made at least in part from a medical grade polymer including a polyether block amide (PEBA), such as PEBAX 55D available from Arkema Inc., or other suitable material. In some exemplary embodiments, curvable tube 110 may include one or more additional materials lining a central lumen to provide one or more of hydrophilicity, hydrophobicity, low friction, or other suitable property. For example, curvable tube 110 may include an interior surface including a polytetrafluoroethylene (PTFE), such as TEFLON available from E.I DuPont de Nemours & CO.

Curvable tube 110 may include one or more additional elements to prevent kinking and/or to allow curvable tube 110 to at least partially retain a curved configuration without a separate retainer device. In an exemplary embodiment, curvable tube 110 includes a coiled wire 119 in a polymer material of a wall. For example, a nitinol, stainless steel, or other suitable coil may be impregnated in curvable tube 110 such that curvable tube 110 is flexible and kink-resistant. In some embodiments, a metallic coil may allow curvable tube 110 to retain a curved configuration when bent or flexed.

Curvable tube 110 is configured to bend between a substantially straight configuration in which first end 111 is linearly distal to second end 112 (FIG. 2A), and one or more curved configurations in which first end 111 is not linearly distal to second end 112 (FIG. 2B). FIG. 2B shows exemplary sheath assembly 100 with curvable tube 110 in various curved configurations. Curvable tube 110 may be curved or bent without substantially kinking or otherwise blocking a central lumen or channel defined by curvable tube 110.

In various exemplary embodiments, curvable tube 110 may be curved between multiple configurations in which curvable tube 110 remains operational and allows passage of an interventional tool, medicine, fluid, or other suitable component through curvable tube 110 between first and second ends 111, 112. In an exemplary embodiment, curvable tube 110 is curvable at least between a substantially straight configuration, a first curved configuration in which the curvable tube 110 forms a 180° curve and a second curved configuration in which the curvable tube 110 forms a 90° curve. In various exemplary embodiments, curvable tube 110 may be configured to provide a maximum curve greater than 180°, and may be curved at any suitable angle between the substantially straight configuration and a configuration exhibiting a maximum curve.

Curvable tube 110 may be characterized by a diameter (D) of an arc formed when in a first curved configuration in which curvable tube 110 forms a 180° curve. In various exemplary embodiments, a diameter (D) of the curve may be between 1 cm and 8 cm, 2 cm and 6 cm, or about 3 cm. For example, a diameter (D) of the curve may be less than 8 cm, less than 6 cm, less than 4 cm, less than 2 cm, or less without kinking or substantially blocking elongate portion 113.

In an exemplary embodiment, sheath assembly 100 includes a retainer 150 configured to retain curvable tube 110 in a desired configuration. In the embodiment illustrated in FIG. 2B, retainer 150 includes a plurality of retention features 151 that may selectively engage one or more portions of curvable tube 110. In an exemplary embodiment, retainer 150 may retain curvable tube 110 in a first curved configuration in which curvable tube 110 forms a 180° curve, and one or more additional curved configurations in which curvable tube 110 is positioned to have a curve as desired for a particular application or treatment location, or to allow a physician or healthcare practitioner to more easily work outside of a radiation field, for example. Curvable tube 110 is readily adjustable by removing from one or more retention features 151, positioning into a desired configuration, and engaging with one or more different retention features 151. In this way, first and second ends 111, 112 may be retained in a particular position and orientation, as described further herein.

Figure 3A:
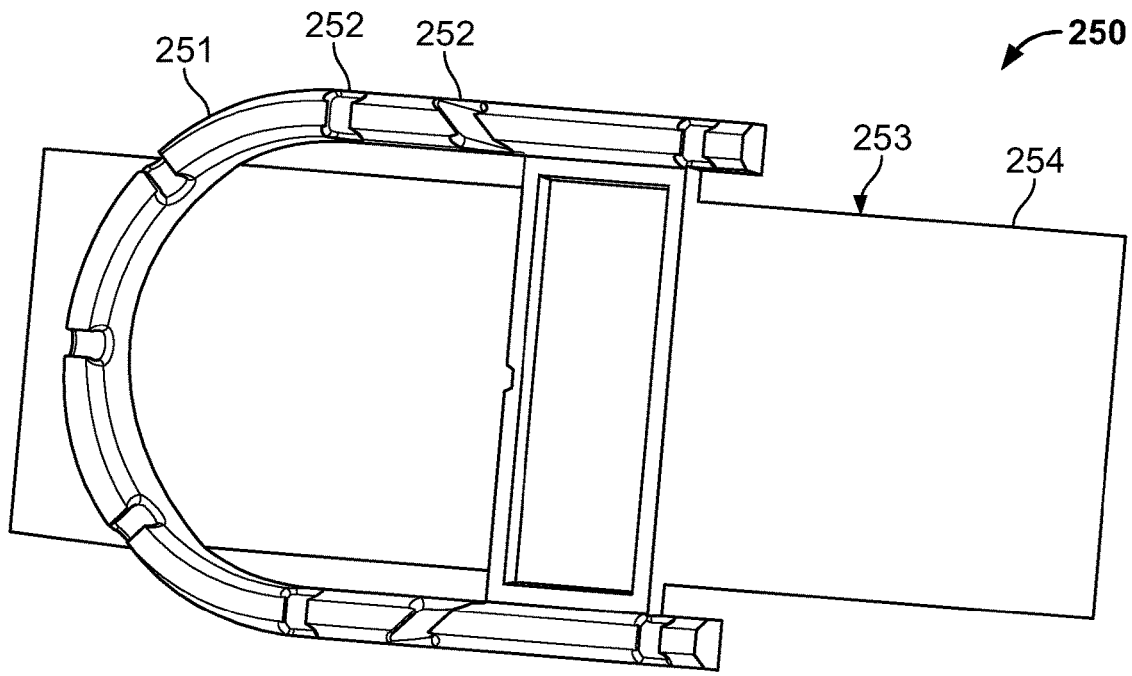
FIGS. 3A-3C show an exemplary retainer device according to the present description.
Figure 3B:
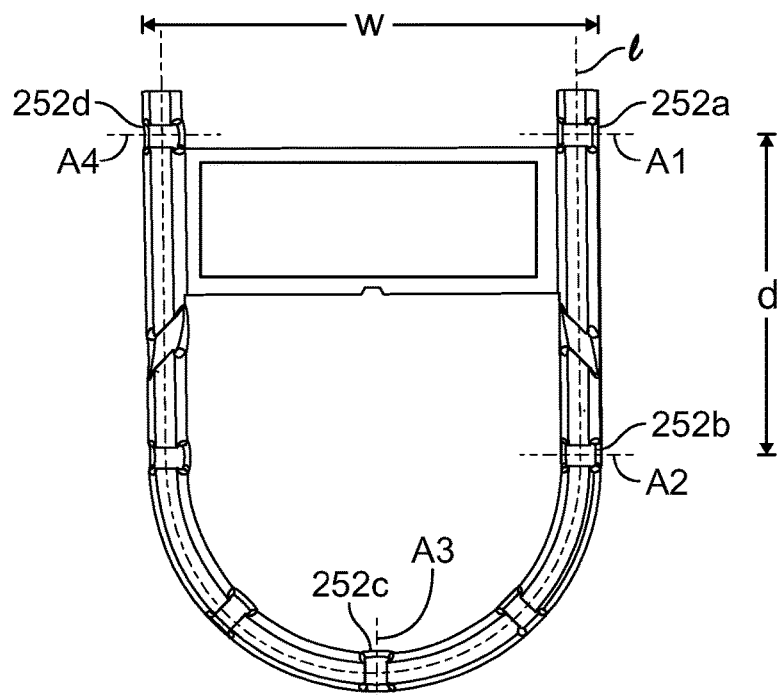
Figure 3C:
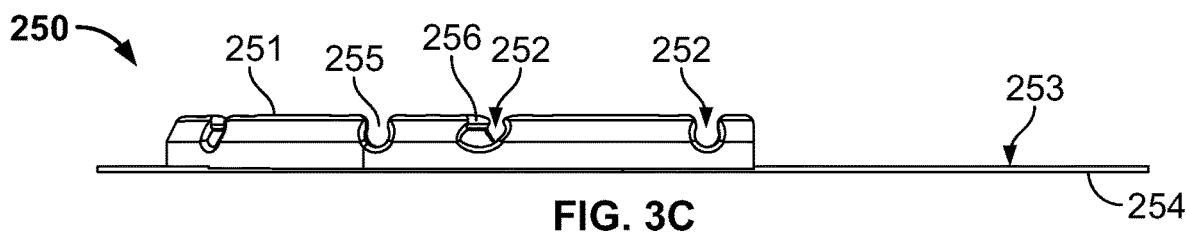

Referring to FIGS. 3A-3C, an exemplary retainer device 250 is shown. In an exemplary embodiment, retainer device 250 includes a frame 251 and one or more retention features 252 configured to hold a curvable portion and/or other components of an exemplary sheath assembly in a selected configuration. Retainer device 250 may be positioned proximate a patient access site, for example, to facilitate handling and use of a sheath assembly.

Retention features 252 may include any suitable feature configured to retain one or more components of a sheath assembly in a desired orientation. In an exemplary embodiment, retention features 252 include one or more channels sized to receive at least a portion of a sheath assembly. For example, retainer device 250 includes a plurality of channels that at least a portion of a sheath assembly may be selectively engaged within. The plurality of channels provide a number of suitable orientations and configurations such that a sheath assembly may be retained in any of multiple curved configurations that range, for example, in selectable increments between 0° to 180°. In various exemplary embodiments, retainer device 250 may include channels spaced and/or oriented in 15°, 30°, 45°, 60°, 90°, or other suitable increments to allow an operator to select a desired configuration.

For example, retainer device 250 may include a first channel 252a and a second channel 252b defining first and second channel axes A1, A2. First and second channel axes A1, A2 are parallel to and offset from one another, and allow portions of a sheath assembly to be retained in first and second channels 252a, 252b such that a portion of the sheath assembly forms a 180° curve. Retainer device 250 may further include a third channel 252c defining a third channel axis A3 that is angled 90° relative to the first channel axis, and a fourth channel 252d defining a fourth channel axis A4 that is coaxial with first channel axis A1. In various exemplary embodiments, retainer device 250 may include one or more channels defining channel axes that are parallel or angled 15°, 30°, 45°, 60°, 115°, 135°, or any other suitable angle, relative to first channel axis A1, respectively.

Retainer device 250 may have any suitable configuration to retain all or a portion of a sheath assembly in a desired configuration. For example, a frame 251 of retainer device 250 may define channels 252 spaced along a perimeter of frame 251. In an exemplary embodiment, frame 251 has a substantially U-shaped configuration. Channels 252 are spaced about the perimeter of frame 251, and one or more channels define channel axes that are orthogonal to the U-shaped frame. For example, U-shaped frame 251 defines a U-shaped central axis 1 passing through a center portion of frame 251. First channel axis A1 is substantially perpendicular to central axis 1, proximate first channel 252a. Similarly, second and third channel axes are substantially perpendicular to frame 251 and central axis 1. In various exemplary embodiments, one or more channels may define channel axes that are angled or not orthogonal relative to central axis 1.

Frame 251 may have any suitable size compatible with a desired curvable tube of a sheath assembly. In an exemplary embodiment, U-shaped frame 251 has an open end 256 having a width w between exterior edges of frame 251 that is less than a length L of a curvable tube retained by retainer 250. In various exemplary embodiments, width w is between 2 cm and 18 cm, 3 cm and 15 cm, 5 cm and 10 cm, or about 6 cm.

Similarly, a distance between various channels 252 may be selected to retain a curvable tube in a desired curved configuration, for example. In an exemplary embodiment, first and second channel axes A1, A2, are fixedly positioned relative to one another and separated by a distance d. In various exemplary embodiments, distance d is between 2 cm and 18 cm, 3 cm and 15 cm, 5 cm and 10 cm, or about 6 cm, and may be the same or different than width w.

In various exemplary embodiments, frame 251 may have any suitable shape that allows retention features, such as channels 252, to retain at least a portion of a sheath assembly in a desired configuration. For example, frame 251 may include half of a U-shaped frame, or may include a circular, square, other suitable shape, or suitable combinations thereof. In some exemplary embodiments, channels 252 may be positioned in a U-shaped pattern, or in another suitable pattern, on a frame 251 that is not U-shaped.

In an exemplary embodiment, retainer 250 includes a base 253. In the embodiment shown in FIGS. 3A and 3C, base 253 includes a substantially planar lower surface 254 that provides stability when retainer device 250 is supported by or attached to a surface. For example, lower surface 254 may include an adhesive and a removable liner. The liner may be removed at a time of use to expose the adhesive of lower surface 254 such that lower surface 254 and retainer device 250 may be adhered to a patient's body, for example proximate an access site, a covering, or other suitable surface where a sheath assembly may be retained. In some example embodiments, lower surface 254 may include a medical grade foam adhesive tape, or other suitable component to adhere retainer device 250 to an appropriate surface. Alternatively or additionally, base 253 may include a textured or non-slip lower surface, or may include a soft or rubberized material. An adhesive or non-slip lower surface 254 maintains retainer device 250 in a desired position and may minimize tension or stress that could otherwise result at a patient access point when a needle, guidewire, or other component, for example, is advanced through curvable tube 310. Retainer device 250 may thus serve as an anchor to maintain a catheter and/or sheath assembly in a stable position relative to a patient access opening.

Referring to FIG. 3C a side view of retainer device 250 is shown. In an exemplary embodiment, at least some of channels 252 include upward facing openings 255 defined by frame 251. Openings 255 allow access to respective channels 252 such that a tube, catheter, sheath, or other suitable component of a sheath assembly may be inserted and retained within a respective channel. In some exemplary embodiments, one or more of channels 252 are sized to frictionally retain a component of a sheath assembly, and for example may have a diameter or major dimension that is similar to or smaller than an outer diameter or major dimension of the component of the sheath assembly. Alternatively or additionally, openings 255 are defined at least in part by a flange or lip 256 such that opening 255 is smaller than a diameter or major dimension of channel 252. A component of a sheath assembly is compressed or deformed while passed through opening 255. The component may be retained in channel 252 until compressed or deformed again to remove from channel 252. Accordingly, a component of a sheath assembly may be readily retained by one or more channels 252.

Frame 251 may be made from any suitable material such that one or more components of a sheath assembly may be retained by retainer device 250. In an exemplary embodiment, frame 251 is integrally formed from a plastic, such as a polyamide. Such a material may provide sufficient stiffness and stability. In some embodiments, retainer device 250 is formed of a material that may not readily be plastically deformed and/or that maintains respective channels 252 fixedly positioned relative to one another. In other exemplary embodiments, retainer device 250 may be bendable or shapable such that frame 251 may be shaped as desired by a physician or healthcare practitioner at a time of use, and will retain its shape when a portion of a sheath assembly is engaged with retainer device 250.

In some exemplary embodiments, frame 251 may be made of a radio-transparent material that does not block or substantially interfere with imaging equipment. A radio-transparent material may thus allow retainer device 250 to be positioned as desired based on operational or ergonomic factors, rather than positioning as may otherwise be necessary to avoid imaging interference.

Referring to FIGS. 4A-4D, an exemplary sheath assembly 300 is shown including a curvable tube 310 and a retainer device 350 in various configurations. Sheath assembly 300 may be configured and positioned as desired for a particular procedure, treatment location, or to provide operational or ergonomic benefits and may be engaged with retainer device 350 to retain the desired configuration and positioning.

Figure 4A:
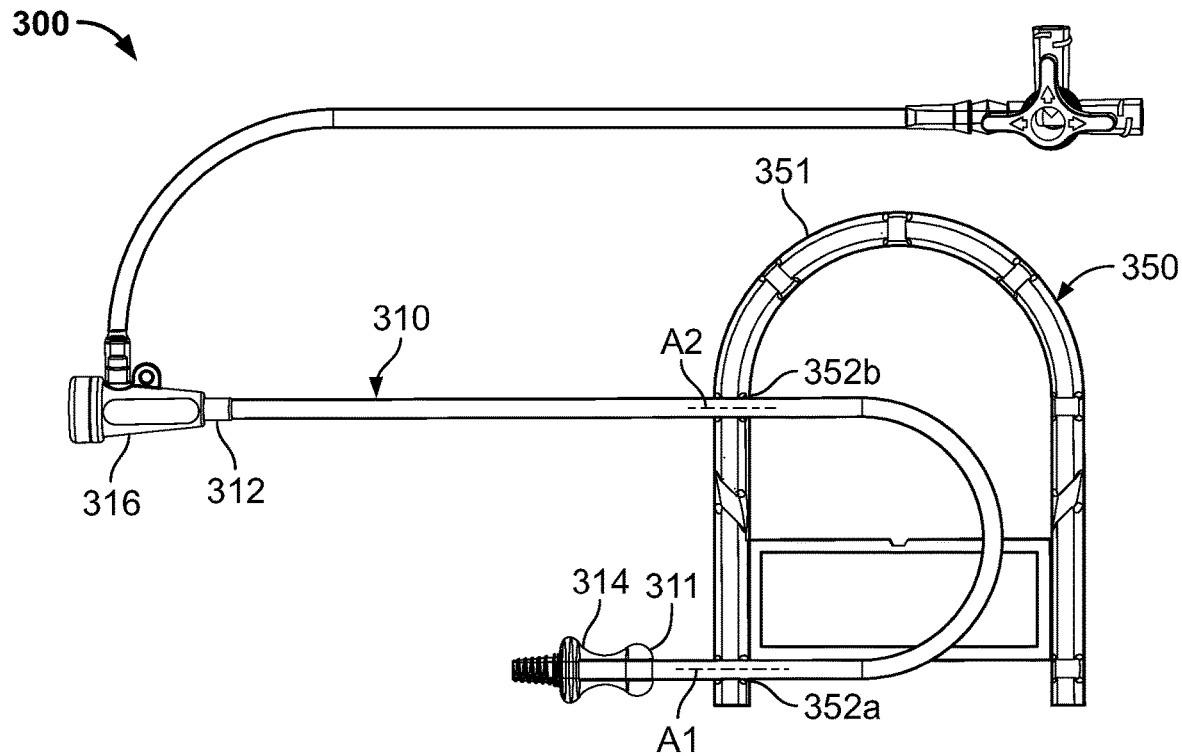
FIG. 4A shows an exemplary retainer device and a curvable tube of a sheath assembly in a 180° curved configuration.

FIG. 4A shows curvable tube 310 of sheath assembly 300 retained in a first curved configuration by retainer device 350. Curvable tube 310 is frictionally retained in first and second channels 352a, 352b defining first and second channel axes A1, A2 that are parallel to and offset from one another. Curvable tube 310 forms a 180° curve such that first and second ends 311, 312, and/or an adapter 314 positioned at first end 311 and port 316 positioned at second end 312 are oriented in substantially the same direction. A physician or healthcare practitioner may insert an interventional tool or other component at port 316 in a first direction such that the interventional tool exits curvable tube 310 into a catheter and/or patient access location in a second direction that is opposite, or rotated 180°, relative to the first direction.

In an exemplary embodiment, at least a portion of curvable tube 310 forming the 180° curve is positioned within a perimeter of retainer device 350. That is, frame 351 forms a U-shaped perimeter, and at least a portion of curvable tube 310 forming the curve is positioned within the U-shaped perimeter. Such positioning may shelter curvable tube 310 and reduce or minimize a possibility of inadvertently catching or snagging on an external object.

Figure 4B:
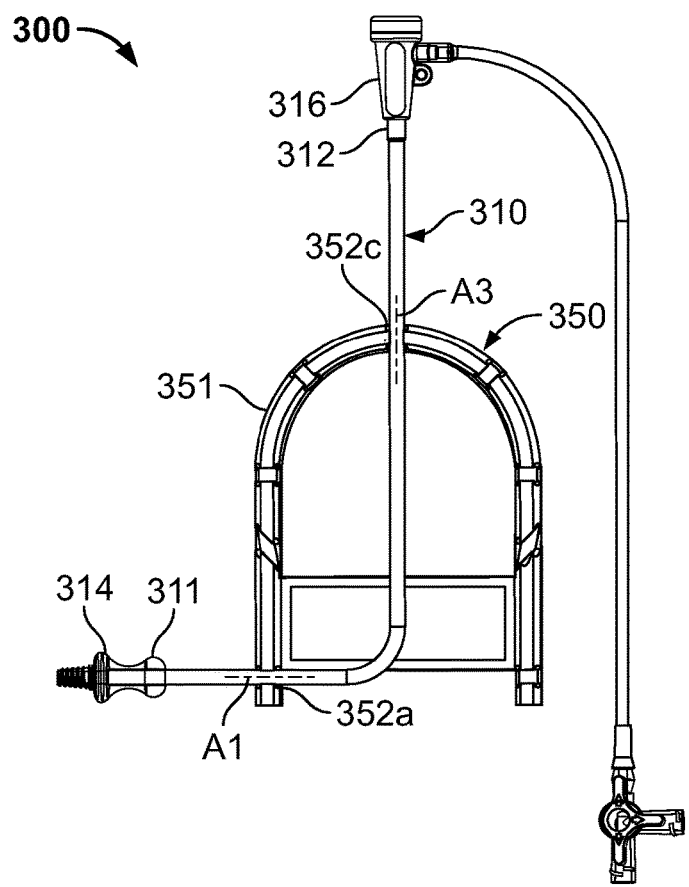
FIG. 4B shows an exemplary retainer device and a curvable tube of a sheath assembly in a 90° curved configuration.

FIG. 4B shows curvable tube 310 of sheath assembly 300 retained in a second curved configuration by retainer device 350. Curvable tube 310 is frictionally retained in first and third channels 352a, 352c defining first and third channel axes A1, A3. Third channel axis A3 is angled 90 relative to first channel axis A1. Curvable tube 310 thus forms a 90° curve such that first and second ends 311, 312, and/or an adapter 314 positioned at first end 311 and port 316 positioned at second end 312 are oriented approximately perpendicularly relative to each other. A physician or healthcare practitioner may insert an interventional tool or other component at port 316 in a first direction such that the interventional tool exits curvable tube 110 into a catheter and/or patient access location in a second direction that is rotated 90° relative to the first direction.

Figure 4C:
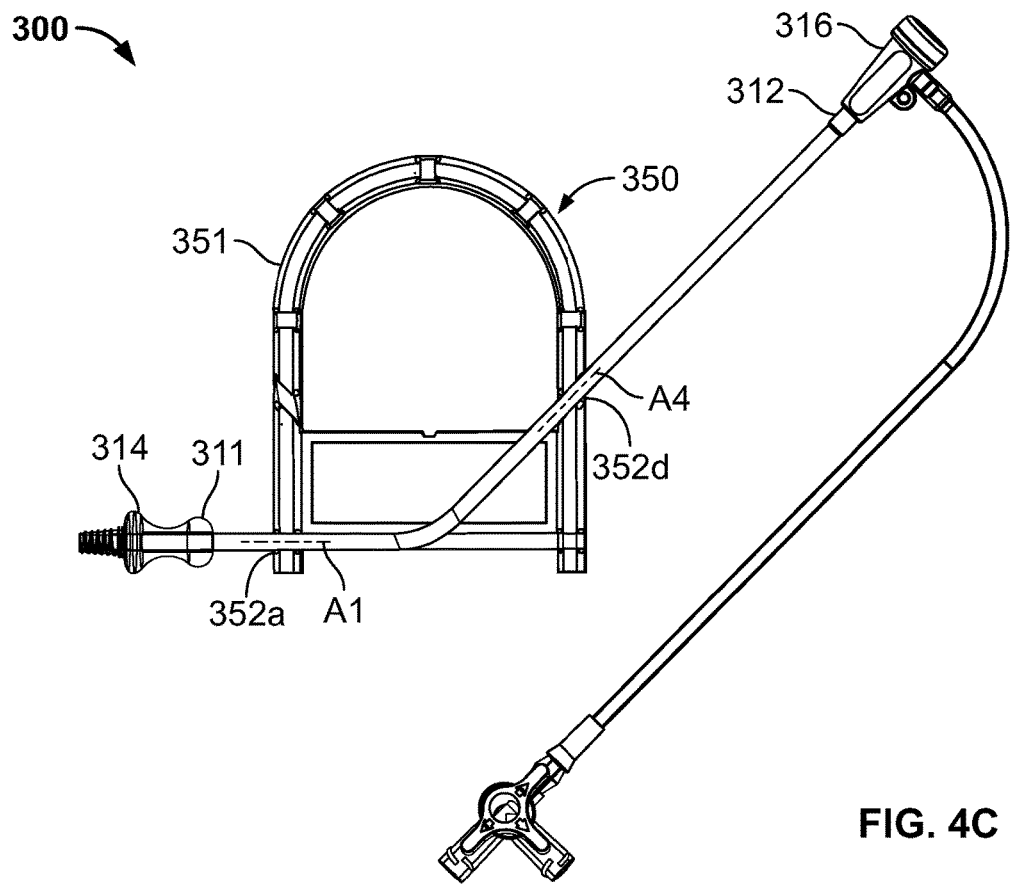
FIG. 4C shows an exemplary retainer device and a curvable tube of a sheath assembly in a 45° curved configuration.

FIG. 4C shows curvable tube 310 of sheath assembly 300 retained in a third curved configuration by retainer device 350. Curvable tube 310 is frictionally retained in first and fourth channels 352a, 352d defining first and fourth channel axes A1, A4. Fourth channel axis A4 is angled 45° relative to first channel axis A1. Curvable tube 310 thus forms a 45° curve such that first and second ends 311, 312, and/or an adapter 314 positioned at first end 311 and port 316 positioned at second end 312 are oriented at an angle of approximately 45° relative to each other. A physician or healthcare practitioner may insert an interventional tool or other component at port 316 in a first direction such that the interventional tool exits curvable tube 110 into a catheter and/or patient access location in a second direction that is rotated approximately 45° relative to the first direction.

Figure 4D:
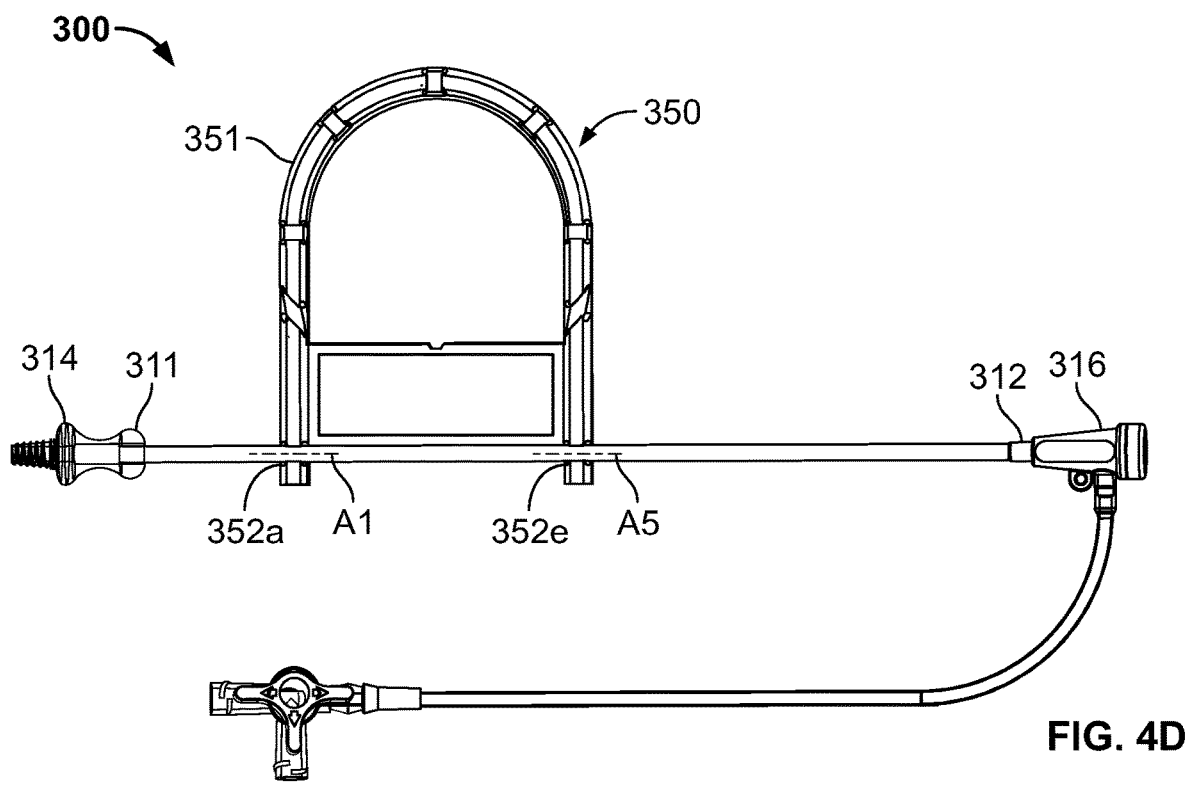
FIG. 4D shows an exemplary retainer device and a curvable tube of a sheath assembly in a straight configuration.

FIG. 4D shows curvable tube 310 of sheath assembly 300 retained in a fourth curved configuration by retainer device 350. Curvable tube 310 is frictionally retained in first and fifth channels 352a, 352e defining first and fifth channel axes A1, A5. Fifth channel axis A5 is coaxial relative to first channel axis A1. Curvable tube 310 thus is retained in a substantially straight configuration in which first end 111 is linearly distal to second end 112. First and second ends 311, 312, and/or an adapter 314 positioned at first end 311 and port 316 positioned at second end 312 are oriented in a substantially linear configuration relative to each other. A physician or healthcare practitioner may insert an interventional tool or other component at port 316 in a first direction such that the interventional tool exits curvable tube 110 into a catheter and/or patient access location in a second direction that is approximately the same as first direction. Curvable tube 310 may act as an extension allowing a physician or healthcare physician to work a greater distance away from a patient access site and/or radiation field.

Retainer device 350 may include any number of additional channels that define channel axes in any suitable orientation. For example, additional channels may be provided to allow curvable tube 310 to be retained in additional configurations. Furthermore, one or more channels may be configured to retain curvable tube 310 in a curved configuration in which curvable tube 310 has multiple curves, to exhibit an S-shaped curve or a serpentine pattern, for example.

Figure 5:
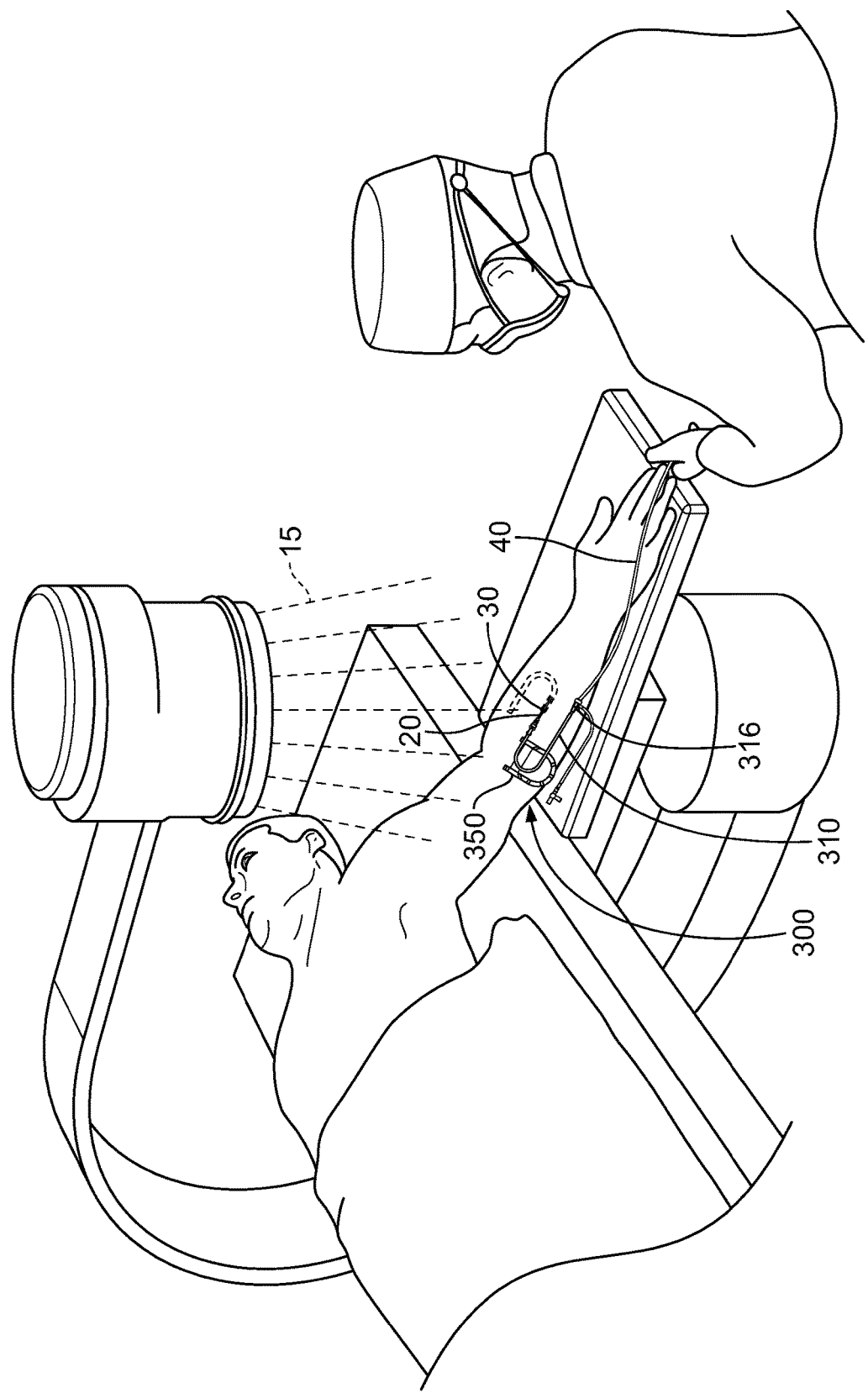
FIG. 5 shows an exemplary sheath assembly in use in a medical environment.

FIG. 5 shows an exemplary sheath assembly 300 in use in a medical environment. Sheath assembly 300 includes a curvable tube 310 in a curved configuration forming a 180° curve. Retainer 350 retains curvable tube 310 in the curved configuration and is adhered, for example to a patient, in a fixed position relative to a patient access point 30. Curvable tube 310 is attached to a catheter 20, such as a peripheral intravenous catheter, extending into the patient's vasculature through an access point 30. Catheter 20 has a septum at a proximal end external to a patient's skin that is configured to releasably mate with an adapter, for example, and defines a pathway for delivery or withdrawal of fluids, instruments such as guide wires or other interventional tools, or a combination thereof into a patient. Catheter 20 and/or the septum may include a hemostasis valve that minimizes back bleeding and prevents introduction of air, while permitting the introduction of fluids or instruments.

In an exemplary embodiment, catheter 20 is inserted into a patient by an operator such as a physician or healthcare practitioner. Sheath assembly 300 is attached by joining first end of curvable tube 310 with a septum, for example, of catheter 21. The operator may select a straight or suitable curved configuration for sheath assembly 300, and maintain the selected configuration by engaging portions of sheath assembly 300 with retainer 350. For example, the operator may position an elongate portion of sheath assembly 300 in one or more channels or other retention features of retainer 350.

In the illustrated embodiment, sheath assembly 300 is retained in a curved configuration including a 180° curve. The operator is able to introduce an interventional tool 40 into port 316 of curvable tube 310 in a first direction towards the patient's abdomen, for example. Interventional tool 40 passes through curvable tube 310 and enters access point 30, directly or indirectly, in a second direction that is opposite, or rotated 180°, relative to the first direction. Curvable tube 310 in a curved configuration thus allows a physician or healthcare practitioner to operate away from a field of radiation 15 and/or while in an ergonomic position. The operator's hands are positioned outside of field of radiation 15 during the operation, and the physician's head, neck and other body part's may be positioned a greater distance from field of radiation 15.

Sheath assembly 300 may be used in any suitable procedure, and may be particularly advantageous in image guided surgery procedures in which access site restraints may inhibit workflow or physician ergonomics and/or expose an operator to radiation. In an exemplary embodiment, sheath assembly 300 may be used in one or more of hemodialysis intervention, arteriovenous fistula (AVF) intervention, antegrade percutaneous arterial intervention of the femoral artery or other vessel, obese patient access, contralateral groin access, electrophysiological cardiology procedures, pacemaker insertions, renal collecting system intervention, ureteral strictures, urinary conduit formation, treatment of the biliary tree, portal venous system, gastrointestinal tract or spinal canal, and/or other suitable applications. In various exemplary embodiments, sheath assembly 300 allows a physician or healthcare practitioner to operate near an extremity and away from a patient's abdomen, chest and head. Similarly, a physician or healthcare practitioner may operate distant from a maximum radiation field that may be directed proximate a patient access site and/or treatment location.

In various exemplary embodiments, sheath assembly 300 provides a modular system that may be used with one or more additional components to provide additional functionality and/or flexibility. For example, curvable tube 310 may be joined, directly or indirectly, with exhalable or detachable appendages. A curvable portion that is larger or having a greater length may be used for larger patients receiving lower extremity intervention, for example. A Toughy-Borst fitting may be used to facilitate simultaneous introduction of a fluid while using a guide wire during catheterization. A double lumen or bifurcated sheath may be used for therapy requiring two wires and access sites. A larger internal diameter may be used to create relatively larger communication for a suction thrombectomy, for example.

A sheath assembly may be provided as a kit including one or more curvable tubes, adapters, and/or retainer devices. An exemplary embodiment of a kit includes a retainer device and first and second curvable tubes having the same or different lengths and/or diameters, such that a physician or healthcare practitioner may customize a sheath assembly at a time of use as desired for a particular patient or treatment. For example, a longer curvable tube may be used to facilitate antegrade access to the femoral artery for peripheral vascular disease treatment of the ipsilateral extremity, and allow the physician or healthcare practitioner to operate proximate a patient's legs rather than a patient's abdomen, for example. A curvable tube having a desired length may allow curvable tube to curve around a patient's leg and towards the feet to provide ergonomic and operational advantages to the physician or healthcare practitioner and patient.

In some exemplary embodiments, two or more curvable tubes may be connected in series to provide a desired length for a particular patient or treatment. For example, a first end of a first curvable tube may be connected to a second end of a second curvable tube to increase a length of the sheath assembly. A length of sheath assembly may thus be customized by a physician or healthcare practitioner at a point of use.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Particular embodiments of the subject matter have been described. Other embodiments are within the scope of the following claims.

What is claimed is:

1. A sheath assembly, comprising:
a curvable tube comprising a first end, a second end, and a lumen extending between the first end and the second end, the second end comprising a port configured to receive an interventional tool for delivery through a patient access opening, the curvable tube configured to bend between a curved configuration and a substantially straight configuration in which the first end is linearly distal to the second end;
a retainer having a plurality of tube retainers configured to releasably retain the curvable tube in a plurality of configurations, and a base configured to anchor the retainer to a support surface, wherein each of the base, the first end of the curvable tube, and the second end of the curvable tube remain in a fixed position relative to the patient access opening while the interventional tool is advanced through the curvable tube and through the patient access opening such that the curvable tube is retained in a selected one of the plurality of configurations;
the plurality of configurations including a first curved configuration in which the curvable tube is releasably retained in a 90° curve by the retainer while the interventional tool is advanced through the curvable tube and through the patient access opening and a second curved configuration in which the curvable tube is releasably retained in a 180° curve by the retainer while the interventional tool is advanced through the curvable tube and through the patient access opening.

2. The sheath assembly of claim 1, wherein when the curvable tube is retained in the first curved configuration the interventional tool is insertable through the port of the curvable tube in a first direction such that the interventional tool exits the first end of the curvable tube in a second direction, the first direction rotated 90° relative to the second direction, while the first and second ends of the curvable tube remain in a fixed position relative to the patient access opening.

3. The sheath assembly of claim 1, wherein the first end of the curvable tube is positionable through the patient access opening.

4. The sheath assembly of claim 1, wherein the first end of the curvable tube comprises a connector.

5. The sheath assembly of claim 1, wherein the tube retainers are fixedly positioned relative to one another.

6. The sheath assembly of claim 1, wherein the base comprises a planar lower surface configured to be attached to a support surface.

7. The sheath assembly of claim 1, wherein the tube retainers comprise a plurality of channels.

8. The sheath assembly of claim 2, wherein when the curvable tube is retained in the second curved configuration the interventional tool is insertable through the port of the curvable tube in a first direction such that the interventional tool exits the first end of the curvable tube in a second direction, the first direction rotated 180° relative to the second direction, while the first and second ends of the curvable tube remain in a fixed position relative to the patient access opening.

9. The sheath assembly of claim 4, further comprising a catheter having a distal end, a proximal end, and at least one lumen that extends between the distal end and the proximal end, the distal end configured to be positioned within a patient, and the proximal end configured to be connected to the curvable tube and positioned outside of a patient during advancement of the interventional tool.

10. The sheath assembly of claim 7, wherein the plurality of channels include a first channel defining a first channel axis and a second channel defining a second channel axis and a third channel defining a third channel axis, the first channel axis coaxial with the second channel axis, the third channel axis angled 45° relative to the first channel axis.

11. The sheath assembly of claim 7, wherein the plurality of channels comprise a first channel defining a first channel axis and a second channel defining a second channel axis, the first channel axis being coaxial with the second channel axis.

12. The sheath assembly of claim 8, wherein the plurality of configurations includes a third curved configuration in which the curvable tube is releasably retained in a 45° curve by the retainer.

13. The sheath assembly of claim 10, further comprising a fourth channel defining a fourth channel axis, the fourth channel axis rotated 90° relative to the first channel axis, wherein the curvable tube is retained in the first and fourth channels when in the first configuration such that the interventional tool is insertable through the port of the curvable tube in a first direction such that the interventional tool exits the first end of the curvable tube in a second direction, the first direction rotated 90° relative to the second direction, while the first and second ends of the curvable tube remain in a fixed position relative to the patient access opening.

14. The sheath assembly of claim 11, wherein the first channel axis and the second channel axis are perpendicular to a central axis of the retainer.

15. The sheath assembly of claim 12, wherein when the curvable tube is retained in the third curved configuration the interventional tool is insertable through the port of the curvable tube in the first direction such that the interventional tool exits the first end of the curvable tube in the second direction, the first direction rotated 45° relative to the second direction, while the first and second ends of the curvable tube remain in a fixed position relative to the patient access opening.

16. A sheath assembly, comprising:
a curvable tube comprising a first end, a second end, and a lumen extending between the first end and the second end, the second end comprising a port configured to receive an interventional tool for delivery through a patient access opening, the curvable tube configured to bend between a curved configuration and a substantially straight configuration in which the first end is linearly distal to the second end;
a retainer having a plurality of tube retainers configured to releasably retain the first end and the second end of the curvable tube in a plurality of configurations, and a base configured to anchor the retainer to a support surface, wherein each of the base, the first end of the curvable tube, and the second end of the curvable tube remain in a fixed position relative to the patient access opening while the interventional tool is advanced through the curvable tube and through the patient access opening such that the curvable tube is retained in a selected one of the plurality of configurations; and further comprising a catheter having a distal end, a proximal end, and at least one lumen that extends between the distal end and the proximal end, the distal end configured to be positioned within a patient, and the proximal end configured to be connected to the curvable tube and positioned outside of a patient during advancement of the interventional tool;
wherein the first end of the curvable tube comprises a connector; and
wherein the connector is permanently affixed with the lumen of the curvable tube.

17. The sheath assembly of claim 16, wherein the proximal end of the catheter comprises a sealable connector having a septum.

18. A sheath assembly, comprising:
a curvable tube comprising a first end, a second end, and a lumen extending between the first end and the second end, the second end comprising a port configured to receive an interventional tool for delivery through a patient access opening, the curvable tube configured to bend between a curved configuration and a substantially straight configuration in which the first end is linearly distal to the second end, the interventional tool insertable through the curvable tube while the curvable tube is in the curved configuration;
a retainer having a plurality of tube retainers configured to releasably retain the curvable tube in a plurality of configurations, the plurality of tube retainers fixedly positioned relative to one another, and a base configured to anchor the retainer to a support surface wherein each of the base and first and second ends of the curvable tube remain in a fixed position relative to the patient access opening such that the curvable tube is retained in a selected one of the plurality of configurations while the interventional tool is advanced through the curvable tube and through the patient access opening, the plurality of configurations including a first curved configuration in which the curvable tube is releasably retained in a 90° curve by the retainer while the interventional tool is advanced through the curvable tube and through the patient access opening and a second curved configuration in which the curvable tube is releasably retained in a 180° curve by the retainer while the interventional tool is advanced through the curvable tube and through the patient access opening;
wherein the interventional tool is insertable through the port of the curvable tube in a first direction such that the interventional tool exits the first end of the curvable tube in a second direction while the curvable tube remains in a position relative to the patient access opening, the first direction rotated relative to the second direction.

19. The sheath assembly of claim 18, wherein the first end of the curvable tube is positionable through the patient access opening.

20. The sheath assembly of claim 18, wherein the first end of the curvable tube comprises a connector.

21. The sheath assembly of claim 18, wherein the base comprises a planar lower surface configured to be attached to a support surface.

22. The sheath assembly of claim 20, further comprising a catheter having a distal end, a proximal end, and at least one lumen extending between the distal end and the proximal end, the distal end configured to be positioned within a patient, and the proximal end configured to be connected to the curvable tube and positioned outside of a patient during advancement of the interventional tool.

* * * * *